United States Patent
Sun et al.

(10) Patent No.: US 7,336,354 B2
(45) Date of Patent: Feb. 26, 2008

(54) SPECTROPHOTOMETER

(75) Inventors: Yin Sheng Sun, Glen Waverley (AU); Martin Keith Masters, Rowville (AU)

(73) Assignee: Varian Australia PTY, Ltd, Mulgrave, Victoria (AU)

(*) Notice: Subject to any disclaimer, the term of this patent is extended or adjusted under 35 U.S.C. 154(b) by 108 days.

(21) Appl. No.: 10/546,886

(22) PCT Filed: Feb. 27, 2004

(86) PCT No.: PCT/AU2004/000249

§ 371 (c)(1),
(2), (4) Date: May 8, 2006

(87) PCT Pub. No.: WO2004/076995

PCT Pub. Date: Sep. 10, 2004

(65) Prior Publication Data

US 2006/0290926 A1    Dec. 28, 2006

(30) Foreign Application Priority Data

Feb. 27, 2003   (AU) ............................. 2003900902

(51) Int. Cl.
*G01J 3/42* (2006.01)
*G01J 3/32* (2006.01)
*G01J 3/443* (2006.01)

(52) U.S. Cl. .................. 356/318; 356/319; 356/326; 356/328; 356/331; 356/334

(58) Field of Classification Search ............. 356/318, 356/319, 331, 334, 326, 328
See application file for complete search history.

(56) References Cited

U.S. PATENT DOCUMENTS 3,606,547 A * 9/1971 Iwahashi .................... 356/325

4,014,612 A * 3/1977 Atwood et al. ............. 356/325

(Continued)

FOREIGN PATENT DOCUMENTS

GB      2116707 A      9/1983

(Continued)

*Primary Examiner*—F. L. Evans
*Assistant Examiner*—Bryan J Giglio
(74) *Attorney, Agent, or Firm*—Bella Fishman

(57) ABSTRACT

A spectrophotometer having an optical system for directing a beam of substantially monochromatic excitation light to a liquid sample contained in a well (3) of a well plate for interaction with the sample for absorption or emission measurements to analyse the sample. The optical system includes two apertures (46, 28) for establishing a Kohler illumination region outside the well, that is an excitation beam region between conjugate images (18, 21) of the two apertures. This excitation beam region is then demagnified and imaged (10, 9) into the well (3). The invention provides for the shape of the Kohler illumination region to correspond to the shape of the well space so that all of the liquid sample is uniformly illuminated without the well obstructing any portion of the illuminating excitation beam of light. Advantages of the invention are that the Kohler illumination region of the excitation beam is convenient for insertion of filters (20), apertures and polarisers (19) into the excitation optical system and permits use of small and thus cheaper filters and polarisers. Also the invention provides for accurate absorption or emission measurements from a liquid sample in a well notwithstanding that the sample may only partially fill the well.

16 Claims, 2 Drawing Sheets

U.S. PATENT DOCUMENTS

| | | | |
|---|---|---|---|
| 4,022,529 A * | 5/1977 | White | 356/318 |
| 4,052,161 A * | 10/1977 | Atwood et al. | 436/34 |
| 4,053,236 A | 10/1977 | Atwood et al. | |
| 4,099,872 A * | 7/1978 | White | 356/318 |
| 4,311,387 A * | 1/1982 | deMey et al. | 356/318 |
| 5,153,679 A * | 10/1992 | Gilby | 356/440 |
| 5,173,742 A | 12/1992 | Young | |
| 5,680,209 A * | 10/1997 | Machler | 356/319 |
| 6,071,748 A * | 6/2000 | Modlin et al. | 436/174 |
| 6,097,025 A * | 8/2000 | Modlin et al. | 250/227.22 |
| 6,469,311 B1 * | 10/2002 | Modlin et al. | 250/576 |
| 6,503,719 B2 * | 1/2003 | Modlin et al. | 435/6 |
| 6,982,431 B2 * | 1/2006 | Modlin et al. | 250/573 |

FOREIGN PATENT DOCUMENTS

| | | |
|---|---|---|
| GB | 2313188 A | 11/1997 |
| JP | 10-246692 A | 9/1998 |

* cited by examiner

SPECTROPHOTOMETER

TECHNICAL FIELD

The present invention relates to a spectrophotometer for the analysis and characterisation of samples by measurement of their absorption or fluorescence spectra, particularly when the analytical samples are liquid samples presented to the spectrophotometer in a well plate.

BACKGROUND OF THE INVENTION

The following discussion of the background to the invention is included to explain the context of the invention. This is not to be taken as an admission that any of the material referred to was published, known or part of the common general knowledge in Australia as at the priority date of any of the claims.

Analytical samples can be characterised and analysed by spectrophotometric measurements of the absorption of light by a sample. Analytical samples can also be characterised and analysed by spectrophotometric measurements of the fluorescence of a sample.

To perform a spectrophotometric measurement of the absorption of light by a sample a source of substantially monochromatic light of a selected wavelength is provided for the purpose of illuminating an analytical sample. Such substantially monochromatic light is conveniently obtained by providing a continuum light source such as a xenon arc lamp or flash lamp and also providing a wavelength selective means such as a grating monochromator between the continuum light source and the analytical sample. A means of detecting and measuring the intensity of the substantially monochromatic light after its passage through an analytical sample in an appropriate sample container is also provided so that the absorption of light by the analytical sample can be measured.

To perform a measurement of the fluorescence of a sample a source of substantially monochromatic light of a first wavelength is similarly provided for illuminating an analytical sample and causing the sample to emit light. The substantially monochromatic light of a first wavelength that illuminates the analytical sample is called the excitation light, and the light emitted by the illuminated analytical sample is called the emission light. A means of selecting from the emission light substantially monochromatic light of a second wavelength is provided and this light is transmitted to a light detecting device for detection and measurement. Such selecting means can be for example a second grating monochromator between the analytical sample and the light detecting device.

Light detecting devices useful in spectrophotometers include photomultiplier tubes, photodiodes and charge-coupled devices. All such devices produce an electrical signal that is proportional to the quantity of light (i.e. to the number of photons per second) reaching the device. It is a characteristic of such light detecting devices that the signal-to-noise ratio is less when the quantity of light failing on the device is less, provided that the quantity of detected light is always sufficiently low that the detecting device is able to operate correctly. In practice, the design of the spectrophotometer ensures that the quantity of detected light is always kept sufficiently low that the detecting device is able to operate correctly. Consequently, the best signal-to-noise ratio is achieved when as much detectable light as possible reaches the detecting device.

To achieve the best signal-to-noise ratio the analytical sample should be uniformly illuminated with the required substantially monochromatic light, and such uniform illumination ideally should be achieved while allowing all the available substantially monochromatic light to enter the sample container and interact with the sample. Any of said light that does not enter the sample container is wasted, and the signal-to-noise ratio of the measurement is less than it might otherwise be. Similarly, it is also desirable that light of interest transmitted through or emitted by the illuminated sample be efficiently collected and transmitted to the light detecting device. Any light of interest that is not collected and transmitted to the light detecting device is wasted, and the signal-to-noise ratio of the measurement is less than it might otherwise be.

Liquid analytical samples are advantageously presented to a spectrophotometer with the aid of a device called a "microplate" or "well plate". These terms are synonymous; for convenience, the term "well plate" will be used herein. A well plate consists of a multiplicity of sample containers rigidly mounted in an array. Movement of the array with respect to the optical path in the spectrophotometer allows each sample in turn to be illuminated with appropriate substantially monochromatic light so that light of interest can be detected and measured. In the case of absorption measurements the light of interest will be light that has passed through the sample. In the case of fluorescence measurements the light of interest will be light that has been emitted by the illuminated sample. This arrangement allows rapid and convenient analysis of a large number of individual analytical samples. A spectrophotometer arranged to operate in this fashion is known as a well plate reader or microplate reader. In order to provide as many sample containers as possible in a well plate of constant area, it is common to make such sample containers much deeper than they are wide. This long, narrow configuration of the sample container introduces difficulties in the illumination of the sample contained therein. It also introduces difficulties in the collection of light of interest from the sample for detection and measurement.

For example, in prior art well plate readers it is common to illuminate the sample with a cone of substantially monochromatic light formed between the focusing component and the focus. The focus is positioned in the well below the surface of the sample. The subtended angle of the cone of light is made as large as possible to maximise the quantity of light provided. The limitation of this arrangement becomes evident when only a limited volume of sample is available and consequently the surface of the sample is considerably below the top of the well. When the focus is positioned below the surface of the sample the top edges of the well obscure some of the light that is intended for illumination of the sample.

When absorbance measurements are being made any obstruction of light by the top edges of the well inevitably reduces the amount of light reaching the absorbance detector and thereby reduces the signal-to-noise ratio of the absorbance measurements.

When fluorescence measurements are being made the quantity of fluorescently emitted light is proportional to the quantity of light illuminating the sample, so any reduction in the quantity of illuminating light is inevitably associated with a reduction in the quantity of light fluorescently emitted by the sample. This in turn reduces the signal-to-noise ratio of the fluorescence measurements.

The prior-art arrangement for collecting fluorescently emitted light is the same as that just described for illumination. This results in a further shortcoming for fluorescence measurements of a sample having a surface considerably below the top of the well. The optical path defined by the collection angle of the fluorescently-emitted light is obscured by the top of the well. The effective collection angle is thereby reduced. This reduces the quantity of light reaching the fluorescence detector by a factor similar to that by which the illumination of the sample is reduced. This results in a further reduction of the signal-to-noise ratio of the fluorescence measurements.

DISCLOSURE OF THE INVENTION

An object of the present invention is to provide a spectrophotometer having improved sensitivity and flexibility for detecting fluorescence, phosphorescence and absorption in liquid samples contained in a well.

Accordingly, in a first aspect the present invention provides a spectrophotometer having an optical system for directing a beam of substantially monochromatic light into a liquid sample in a well, the optical system including a first aperture and a second aperture and focussing means for forming conjugate images of the first and the second apertures outside of the well to establish therebetween a beam region of monochromatic light, wherein the first and second apertures are sized and shaped for said beam region to have a shape that is similar to the internal shape of the well, and imaging means for imaging said region of the beam to a size corresponding to the internal size of the well at the well for the imaged said region of the beam of monochromatic light to illuminate substantially all of the liquid sample in the well without the well obstructing any portion of the imaged said region of the beam.

The arrangement to provide the conjugate images to establish the region of the beam of light of similar shape is an example of "Kohler illumination" conjugation. It provides the most uniform and limited-glare illumination with minimal energy loss in the system. The region of similar shape between the conjugate images also advantageously provides for convenient insertion of filters, apertures and polarisers and permits the use of small filters and polarisers, which are normally more cost effective than larger ones.

A Kohler illumination conjugation region that is of substantially constant cross-section is preferably established because this suits the normal internal shape of the wells in a well plate, i.e. it suits a well that is parallel walled and has a greater depth than width. However, given that the three dimensional shape of the Kohler illumination conjugation region depends on the shape and size of the images of the two apertures that establish the region, which in turn depends upon the shape and size of the first and second apertures, it is to be understood that those apertures may be shaped and sized to establish a Kohler illumination conjugation region that is appropriately shaped to suit a differently shaped well. For example, for a well having inwardly tapered walls a Kohler illumination conjugation region of frustoconical shape could be established by appropriately shaping and sizing the first and second apertures.

A particular advantage of the invention (as will be described in more detail hereinbelow) is that it allows for accurate measurement of an analytical sample in a well notwithstanding that the sample does not fill the well.

Preferably the focussing means for providing the Kohler illumination conjugation region is a telecentric mirror (i.e. one in which the chief rays are parallel to one another).

Preferably the imaging means for demagnifying and imaging, that is coupling, the Kohler illumination conjugation into the well space is an off-axis ellipsoidal mirror. This mirror performs demagnification volumetric imaging in the optical system. It reduces the three-dimensional region of the beam of substantially monochromatic light into the well of, for example, a 384 multi-well plate without clipping on the wall of the well. This volumetric conjugation imaging provides two main advantages. Firstly, substantially all the liquid sample in the well is uniformly illuminated with limited glare because the volumetric imaging couples the Kohler illumination conjugation into the well space. Secondly, the focussing is insensitive to the height of sample in the well because the beam in the well is of a substantially cylindrical or rectangular parallelepiped shape (depending upon the shape of the apertures), which illuminates the sample in the entire depth of the well with minimal intensity change.

The means for providing the substantially monochromatic light is preferably a monochromator, in which case the first aperture is an entrance slit of the monochromator and the second aperture is the aperture of the diffraction grating of the monochromator. Alternatively the means for providing the substantially monochromatic light may be an optical band pass filter, and the first and second apertures are appropriate apertures on either side thereof, or a prism, also with appropriate apertures to provide the first and second apertures.

The spectrophotometer will include a detection system which may be a system for absorbance measurements, that is, for detecting residual light of the substantially monochromatic beam of light that emerges from the liquid sample, for example through a transparent base of the well.

Alternatively the detection system may be for fluorescence and/or phosphorescence measurements. A spectrophotometer according to the invention may include a detection system for absorption and a detection system for fluorescence/phosphorescence measurements.

A fluorescence/phosphorescence detection system preferably includes an optical system (hereinafter emission optical system) in which the imaging means performs magnification volumetric imaging of the well volume to establish a substantially constant cross-section region of the emission light, this region being established between, in the direction of light travel, an image of the bottom of the liquid sample in the well and an image of the top surface of the liquid sample in the well, with for example an approximate 1:3 transverse magnification. This region allows the insertion into the emission optical system of emission filters, polarisers and apertures of minimal physical size.

Preferably the emission optical system includes focussing means, such as for example a telecentric mirror, for transferring said three-dimensional emission light region into an emission monochromator. Such focussing means re-images the image of the bottom surface of the well in conjugation with the exit slit of the emission monochromator and the image of the top surface of the well in conjugation with the grating aperture of the emission monochromator. This arrangement follows the Kohler illumination conjugation example (previously described) and ensures that the emission from the liquid sample in the well can be collected with maximised collecting power with minimal energy loss in the emission optical path. It also minimises the variation of the collecting power for light emitted at different positions in the well.

An advantage of a spectrophotometer according to the invention is that an optical system thereof that is optimised for a specific type of well plate (such as for example a plate having 384 wells) can be easily modified to measure a different type of well plate (such as for example a plate having 1536 wells) in which the wells have a different aspect ratio. Simply inserting an appropriate pair of apertures into the constant cross-section region of the excitation optics can provide a beam size to suit a smaller diameter well such as that of the 1536 well plate. This configuration is also suitable for absorption measurements.

The invention encompasses a spectrophotometer that provides for a Kohler illumination conjugation region in the emission optical system (as just described) either with or without a similar Kohler illumination conjugation region in the excitation optical system. Thus according to a second aspect, the invention provides a spectrophotometer including a light source,
a sample position,
an excitation optical system for directing a beam of substantially monochromatic light derived from the light source to a liquid sample when contained in a well when located at the sample position,
and an emission optical system and a detector, the emission optical system for directing light emitted from the liquid sample after interaction of the beam of substantially monochromatic light therewith to the detector,
the emission optical system including
(i) imaging means for providing an image of the bottom surface of the well and an image of the top surface of the liquid sample in the well whereby there is established outside of the well and between the images a region of the emitted light having a shape that is similar to the internal shape of the well,
(ii) focussing means and means for providing substantially monochromatic light from the emission light, the focussing means for focussing the region of emitted light of similar shape onto the means for providing substantially monochromatic light,
the detector arranged to detect the substantially monochromatic emission light from the means for providing such light.

For a normally shaped well, that is one that is parallel walled and has a greater depth than width, the region of the emitted light of similar shape will have a substantially constant cross section. If the shape of the internal space of the well is cylindrical, then the similar shape of said region of the emitted light will be cylindrical.

Preferably the imaging means for magnifying and imaging the well volume to establish said region of the emission light of similar shape is an off-axis ellipsoidal mirror. Preferably the focussing means is a telecentric mirror and the means for providing the substantially monochromatic emission light is a monochromator, although it could instead be a prism or an optical bandpass filter.

For a better understanding of the invention and to show how it may be performed, a preferred embodiment thereof will now be described, by way of non-limiting example only, with reference to the accompanying drawings.

DESCRIPTION OF PREFERRED EMBODIMENT

Figure 1A:
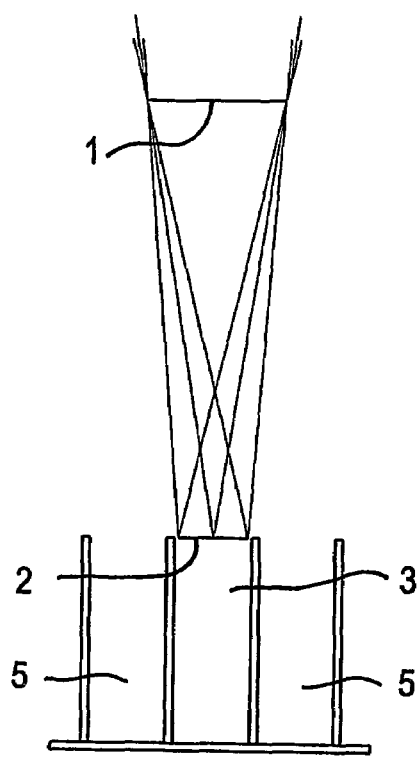
FIGS. 1A and 1B schematically show prior art slit or grating imaging for illuminating a sample in a well.

According to a preferred embodiment, a spectrophotometer includes a spectrophotometer including
a light source,
a sample position,
and an optical system for directing a beam of substantially monochromatic light derived from the light source to a liquid sample when contained in a well when located at the sample position, the well having an internal shape,
the optical system including,
(i) for deriving the beam of substantially monochromatic light, an entrance aperture followed by a second aperture associated with means for providing the substantially monochromatic light,
(ii) focussing means for providing conjugate images of the entrance and second apertures whereby there is established between the conjugate images a region of the beam of substantially monochromatic light that has a particular shape as determined by the shape and size of the conjugate images, and
(iii) imaging means for demagnifying and imaging the region of the beam of light of particular shape into the well for interaction with the liquid sample therein, wherein the particular shape of the region of the beam of light corresponds with the internal shape of the well for substantially all of the liquid sample to be uniformly illuminated without the well obstructing any portion of the beam of light, the spectrophotometer further including a detection system for detecting light from the liquid sample after interaction of the substantially monochromatic beam of light therewith.

The following Legend applies to FIGS. 1A and 1B, 2A and 2B and 3:

1 is a second image of an excitation diffraction grating 28
2 is a second image of the entrance slit 46 of an excitation monochromator 29
3 is a target well
4 (not used)
5 are wells adjacent to target well 3
6 (not used)
7 is the optics for an absorption detector 8
8 is an absorption detector
9 is an off-axis ellipsoidal mirror
10 is a large flat (plane) mirror
11 is a main beam splitter
12 is a beam splitter for a fluorescence reference detector 16
13 is a first attenuator
14 is a curved mirror for a fluorescence reference detector 16
15 is a second attenuator
16 is a fluorescence reference detector
17 is a beam splitter for an absorbance reference detector 23
18 indicates the position of a first image of an entrance slit 16 of an excitation monochromator 29
19 is an excitation polariser
20 is an excitation filter
21 indicates the position of a first image of the ruled surface of an excitation diffraction grating 28 of excitation monochromator 29
22 is a curved mirror for an absorbance reference detector 23
23 is an absorbance reference detector
24 is a focusing mirror (excitation)

25 is a flat (plane) mirror (source optics)
26 is a lens (source optics)
27 is a xenon arc flash lamp
28 is the ruled surface of an excitation diffraction grating of excitation monochromator 29
29 is an excitation monochromator
30 is a collimating mirror of excitation monochromator 29
31 is a focusing mirror of excitation monochromator 29
32 is a collimating mirror of an emission monochromator 34
33 is a focusing mirror of the emission monochromator 34
34 is an emission monochromator
35 is the ruled surface of an emission diffraction grating of emission monochromator 34
36 is a curved mirror for an emission detector 37
37 is an emission detector
38 is a focusing mirror (emission)
39 indicates the position of an image of the top of target well 3
40 is an emission filter
41 is an emission polariser
42 indicates the position of an image of the bottom of target well 3
43 (not used)
44 (not used)
45 is an attenuator for the absorbance reference detector 23
46 is an entrance slit of the excitation monochromator 29
47 is an exit slit of the excitation monochromator 29
48 is an entrance slit of the emission monochromator 34
49 is an exit slit of the emission monochromator 34.

The optical throughput of a spectrophotometer according to an embodiment of the invention is dependent on two apertures of a monochromator: the aperture of the entrance slit and the aperture of the grating, or conjugation images of this pair. The system throughput can be calculated by:

$$T_{sys} = A_s \times A_g / F^2$$

or $$T_{sys} = A_{si} \times A_{gi} / L^2$$

where
$A_s$—the aperture area of the entrance slit
$A_g$—the aperture area of the grating
F—the focal length of the monochromator
$A_{si}$—the image area of the aperture of the entrance slit
$A_{gi}$—the image area of the aperture of the grating
L—the distance between of two images The top aperture and bottom apertures of the well in a well plate reader limit the maximum throughput of light supplied into or collected from a well. The maximum throughput of the well can be calculated by:

$$T_{well} = A_t \times A_b / D^2$$

where
$A_t$—the top aperture area of the well
$A_b$—the bottom aperture area of the well
D—the depth of the well When the throughput of the system is properly matched with the maximum throughput of the well, i.e. $T_{sys} = T_{well}$, optimal system efficiency is achieved. However, if the $T_{sys} > T_{well}$, then a part of the throughput from the system is wasted. If the $T_{sys} < T_{well}$, the volume of the well is not fully illuminated.

In the presented invention, the system has reached optimal efficiency, i.e. $T_{sys} = T_{well}$.

Figure 1B:
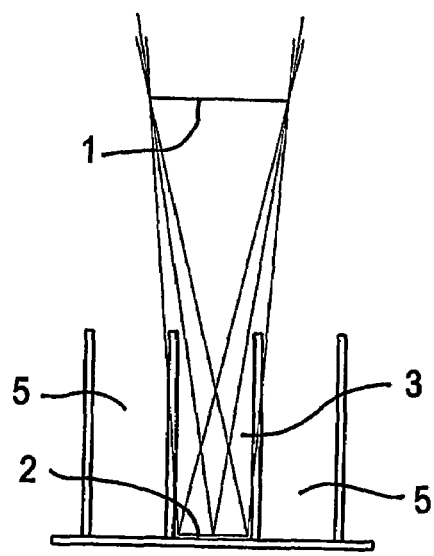

In FIG. 1A, a prior art optical system produces a second image 2 of the entrance slit of an excitation monochromator which is positioned at the top of the well 3 with its size substantially the same as that of the bottom of the well 3. The second image 1 of the grating of the excitation monochromator is positioned at a distance that is twice the depth of the well 3 from the second image 2 of the entrance slit. According to the optimal condition of $T_{sys} = T_{well}$, the entire throughput of the excitation optical system can be transferred into the well 3 and the emission from the entire well 3 can be collected by an emission optical system. In FIG. 1B, however, when the bottom of the well 3 moves closer to the second image 2 of the entrance slit, the top aperture of the well 3 blocks a section of the throughput of the excitation optical system out of the well 3. The geometrical optics of FIG. 1 is therefore not efficient even when the condition of $T_{sys} = T_{well}$ is met.

Figure 2A:
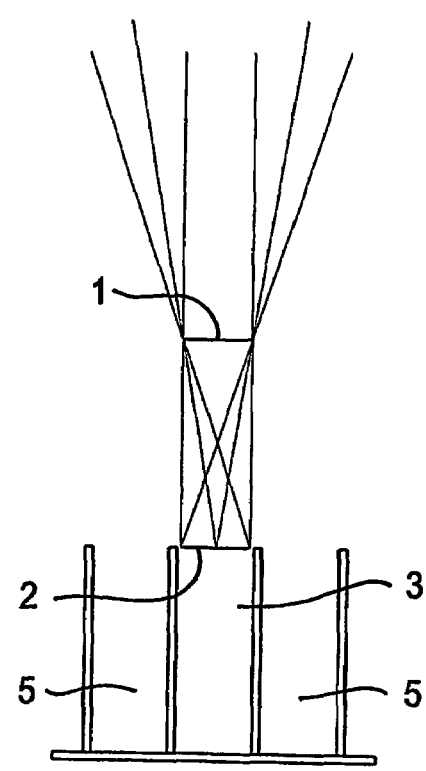
FIGS. 2A and 2B schematically show slit or grating imaging as occurs in a sample well in an embodiment according to the invention.
Figure 2B:
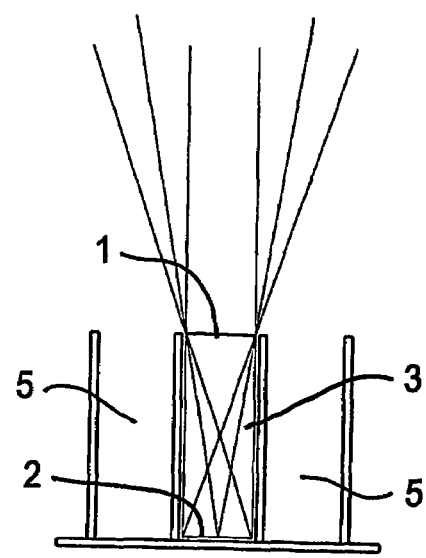
Figure 3:
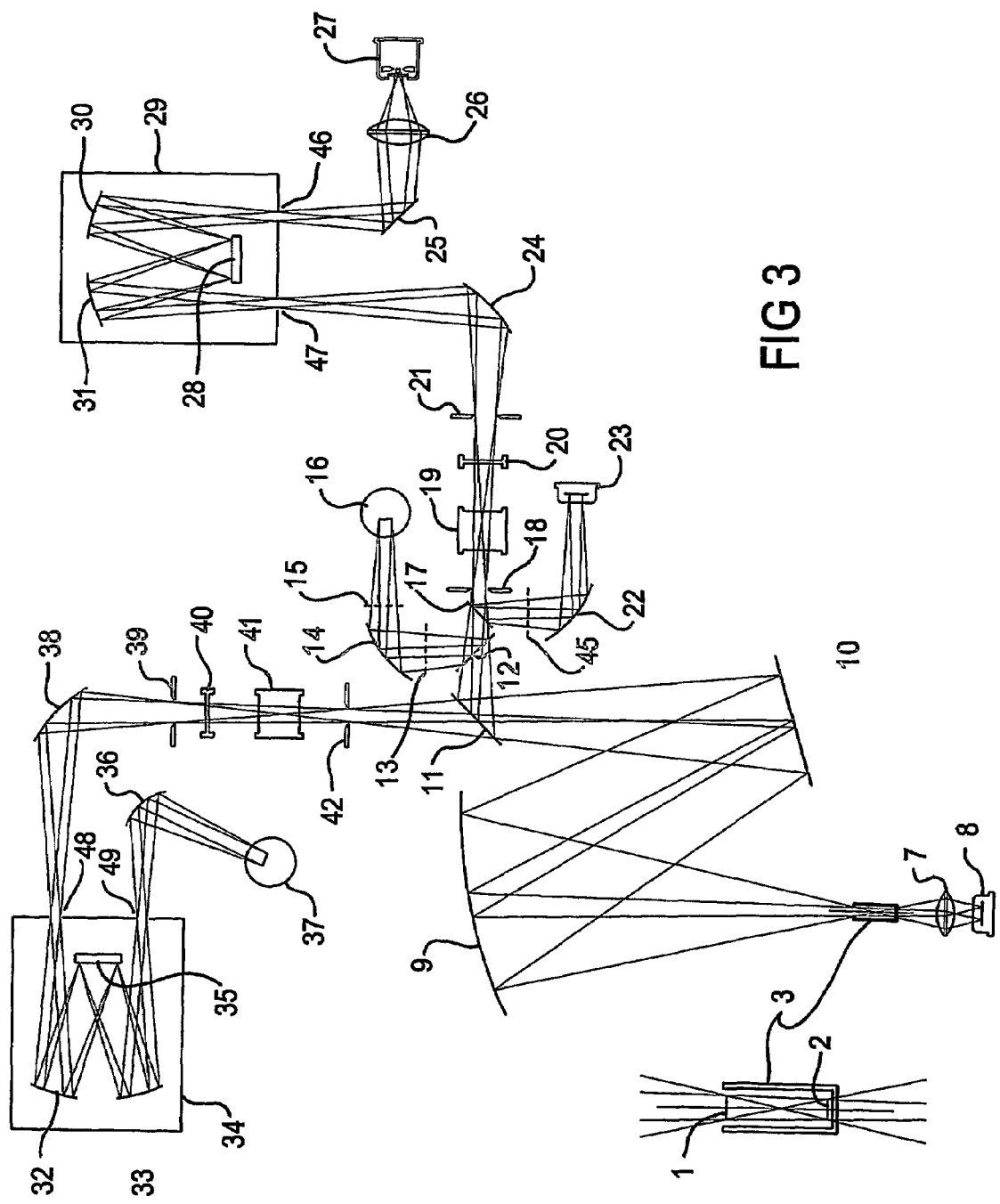
FIG. 3 schematically illustrates a spectrophotometer according to a preferred embodiment of both aspects of the invention.

In FIG. 2A, the optical system of a spectrophotometer according to an embodiment of the invention as shown in FIG. 3 produces a second image 2 of the entrance slit 46 of excitation monochromator 29 which is positioned at the top of the well 3 with its size substantially the same as that of the bottom of the well 3. The second image 1 of the grating 28 of excitation monochromator 29 is positioned at a distance that is substantially the same as the depth of the well 3 from the second image 2 of the entrance slit 46. According to the optimal condition of $T_{sys} = T_{well}$, the entire throughput of the excitation optical system can be transferred into the well 3 and the emission from the entire well 3 can be collected by the emission optical system. In FIG. 2B, when the bottom of the well 3 moves closer to the second image 2 of the entrance slit 46, the top aperture of the well 3 does not block any part of the throughput of the system. The geometrical optics in FIGS. 2A and 2B is therefore more efficient than the prior art system shown in FIGS. 1A and 1B. Furthermore a well plate reader according to an embodiment of the invention is able to function efficiently even when only a small fraction of target well 3 is filled with sample.

Referring now to FIG. 3, light from source 27 (preferably a xenon flash lamp) is focussed by source optics comprising lens 26 and flat mirror 25 onto entrance slit 46 of excitation monochromator 29. Light emerging from slit 46 falls on collimating mirror 30 and is thereby made into a substantially parallel beam that falls on ruled surface 28 of a diffraction grating. Dispersed light from the ruled surface 28 strikes focussing mirror 31 and is brought to a focus forming a substantially monochromatic image of entrance slit 46 at exit slit 47 of excitation monochromator 29. Substantially monochromatic light emerging from exit slit 47 falls on focussing means 24, for example a telecentric mirror 24. Mirror 24 forms an image 21 of ruled surface 28 and an image 18 of entrance slit 46 in a Kohler illumination arrangement. The entrance slit 46 and aperture of grating 28 constitute an first aperture and second aperture according to the invention. If required a filter 20 and/or polariser 19 are advantageously placed in the substantially constant narrow light beam region between images 21 and 18. (Note that although references 18 and 21 illustrate stops, such stops are not necessary in that the embodiment merely involves the respective images being established at the positions of 18 and 21). The small size of the narrow light beam region between 21 and 18 allows physically small filters or polarisers to be used, with corresponding savings in cost.

Light from image 18 falls on a first beam splitter 17. A first portion of this light is reflected from the first beam splitter 17 through attenuator 45 and onto curved mirror 22 that brings the first portion of light to a focus forming an image of ruled surface 28 on absorbance reference detector 23. The electrical signal from reference detector 23 is used as a reference for absorbance measurements and thus compensates for variations in the intensity of source 27. A second portion of the light from image 18 passes through first beam splitter 17 and falls on a second beam splitter 12. A first portion of the second portion of the light is reflected from the second beam splitter 12 through a first attenuator 13 and onto a curved mirror 14 that reflects the first portion of the second portion of light through a second attenuator 15 and brings it to a focus on a fluorescence reference detector 16. A second portion of the second portion of light passes through the second beam splitter 12 and falls on a third beam splitter 11 (the main beam splitter).

Light reflected from the third or main beam splitter 11 falls on a large flat mirror 10 and is reflected therefrom onto an off-axis ellipsoidal mirror 9 that focuses it in target well 3 as previously explained with reference to FIG. 2B. The off-axis ellipsoidal mirror 9 constitutes an imaging means according to the invention.

Absorbance Measurements

Light emerging from the transparent base of target well 3 is brought to a focus by absorption detector optics 7 onto absorbance detector 8. The electrical signal from absorbance detector 8 is used in conjunction with the electrical signal from absorbance reference detector 23 to generate a measurement of the absorbance of a test solution (not shown) in target well 3.

Fluorescence/Phosphorescence Measurements

If a test solution in target well 3 emits light fluorescently when illuminated as just described, fluorescently emitted light collected from the sample emitted follows the same path, but in the opposite direction, as described above for light travelling from main beam splitter 11 to target well 3. A portion of the fluorescently emitted light passes through the main beam splitter 11 and forms an image 42 of the bottom of target well 3 and an image 39 of the top of target well 3. The narrow emission light beam region between images 42 and 39 forms a Kohler illumination arrangement as previously described for the excitation light beam between images 21 and 18. Again, if required a filter 40 and/or polariser 41 are advantageously placed in the narrow emission light beam region between images 42 and 39. (Note that although references 42 and 39 illustrate stops, such stops are not necessary in that this embodiment of the invention merely involves the respective images being established at the positions of 42 and 39). The small size of the narrow emission light beam region allows physically small filters or polarisers to be used, with corresponding savings in cost.

Light from image 39 falls on focusing mirror 38, for example a telecentric mirror, which brings it to a focus on entrance slit 48 of emission monochromator 34. Light emerging from slit 48 falls on collimating mirror 32 and is thereby made into a substantially parallel beam that falls on ruled surface 35 of a diffraction grating of emission monochromator 34. Dispersed light from the ruled surface 35 strikes focussing mirror 33 and is brought to a focus forming a substantially monochromatic image of entrance slit 48 at exit slit 49 of emission monochromator 34. Substantially monochromatic light emerging from exit slit 49 falls on focussing mirror 36 and is brought to a focus on fluorescence detector 37. The electrical signal from fluorescence detector 37 is used in conjunction with the electrical signal from fluorescence reference detector 16 to generate a measurement of the fluorescence of the test solution (not shown) in target well 3.

When an embodiment of a spectrophotometer according to the invention is used to carry out measurements of fluorescently emitted light as just described, the samples are preferably presented in wells having opaque bottoms to prevent reflection of light from the absorbance optics 7 and detector 8 onto mirror 9 and thus ultimately into emission monochromator 34 where it would be a potential source of stray light. It is, however, feasible to use wells having transparent bottoms and to make absorbance and fluorescence measurements on the same sample. The usefulness of such measurements is limited by the fact that a fluorescent sample of sufficient concentration to give a useful absorbance signal would normally generate an excessive fluorescence signal.

Results of a Test of a Spectrophotometer According to the Invention

The detection limit is an important figure of merit for an analytical instrument. The detection limit is defined as the concentration of a specified substance that can be detected with a specified level of confidence under specified conditions. The detection limit is commonly specified as the concentration that gives a signal equal to three times the standard deviation of the signal from a series of measurements of a sample that does not contain the specified substance. The lower the detection limit, the better.

An advantage of the invention is that detection limits measured on samples that do not completely fill a well in a well plate are superior to those found with the prior art. The reason for this is the superior signal-to-noise ratio arising from more efficient illumination of such samples and from more efficient collection of fluorescently emitted light from such samples, as already explained.

As an illustration of the improvements in detection limits achieved by use of a spectrophotometer according to the invention, Table 1 shows the limits of detection for fluorescein calculated from results of fluorescence measurements of a test solution containing 10 picomoles of fluorescein per litre using first, a prior art well plate reader (corresponding to FIG. 1) and second, a well plate reader corresponding to FIG. 2. In each case the test solution placed in a well 3 in a well plate having 384 wells, a 50/50 beam splitter 11 was used and measurements were made using 10 cycles of 30 flashes. When a 100 microlitre sample of test solution was used, the well was nearly full and the detection limits were the same for each instrument. When the sample volume was reduced to 50 microlitres, the well 3 was only about half full. The detection limit with the spectrophotometer instrument according to an embodiment of the invention deteriorated by a factor of two, but that with the prior art instrument deteriorated by a factor of six. This illustrates the advantage of the invention over the prior art in making measurements of low concentrations of substances of interest in limited volumes of sample solution.

Theoretical considerations indicate that reducing the volume of illuminated sample by a factor of two should ideally cause the signal-to-noise ratio (and thus the detection limit) to deteriorate by a factor of two, if the sample is completely illuminated and the collection efficiency of the fluorescently emitted light remains unchanged. Such a deterioration in the detection limit by a factor of two was observed with the spectrophotometer instrument according to an embodiment of the invention. With the prior-art instrument, however, the deterioration was much worse (a factor of six, instead of a factor of two).

TABLE 1

Detection limits for fluorescein in a well plate having 384 wells.

| Instrument | Detection limit with a 100 microlitre sample | Detection limit with a 50 microlitre sample |
|---|---|---|
| Prior art | $5 \times 10^{-13}$ M | $3 \times 10^{-12}$ M (ie. $30 \times 10^{-13}$) |
| According to the invention | $5 \times 10^{-13}$ M | $1 \times 10^{-12}$ M (ie. $10 \times 10^{-13}$) |

It is to be understood that where reference if made to a monochromator in the above description, the monochromator may be replaced by an optical filter, or an optical filter may be used in conjunction with the monochromator. Furthermore, it is to be understood that any monochromator may be double or single. It is also to be understood that the invention is not limited to optical systems using the specific type of monochromator that is shown in FIG. 3 to illustrate the invention. It is to be understood that the invention is also applicable to optical systems using other types of monochromators.

The invention described herein is susceptible to variations, modifications and/or additions other than those specifically described and it is to be understood that the invention includes all such variations, modifications and/or additions which fall within the scope of the following claims.

What is claimed is:

1. A spectrophotometer comprising:
   an optical system for directing a beam of substantially monochromatic light into a liquid sample in a well, the optical system comprising:
   a first aperture and a second aperture and focussing means forming conjugate images of the first and the second apertures outside of the well to establish therebetween a beam region of monochromatic light, wherein the first and second apertures are sized and shaped for said beam region to have a shape that is similar to the internal shape of the well; and
   imaging means imaging said region of the beam to a size corresponding to the internal size of the well at the well for the imaged said region of the beam of monochromatic light to illuminate substantially all of the liquid sample in the well without the well obstructing any portion of the imaged said region of the beam.

2. The spectrophotometer as claimed in claim 1, wherein conjugate images of the first and second apertures are of substantially equal size whereby said region of the beam of light is of substantially constant cross section.

3. The spectrophotometer as claimed in claim 1, wherein the focussing means providing the conjugate images of the first and second apertures is a telecentric mirror.

4. The spectrophotometer as claimed in claim 1, wherein the imaging means imaging said region of the beam of light into the well is an off-axis ellipsoidal mirror.

5. The spectrophotometer as claimed in claim 1, comprising a monochromator providing the beam of substantially monochromatic light, whereby said first aperture is an entrance slit of the monochromator and the second aperture is the aperture of a diffraction grating thereof.

6. The spectrophotometer as claimed in claim 1, further comprising an emission optical system and a detector detecting fluorescently or phosphorescently emitted light from the liquid sample, the emission optical system further comprising:
   (i) imaging means providing an image of the bottom surface of the well and an image of the top surface of the liquid sample in the well whereby there is established outside of the well and between said images of the well and liquid sample a region of the emitted light having a shape that is similar to the internal shape of the well,
   (ii) focussing means and means providing substantially monochromatic light from the emission light, the focussing means focussing the region of emitted light of similar shape onto the means providing substantially monochromatic light;
   the detector is arranged to detect the substantially monochromatic emission light from the means providing such light.

7. The spectrophotometer as claimed in claim 6, wherein the region of the emitted light of similar shape has a substantially constant cross-section.

8. The spectrophotometer as claimed in claim 6, wherein the imaging means providing the images to establish the region of emitted light of similar shape is an off-axis ellipsoidal mirror.

9. The spectrophotometer as claimed in claim 6, wherein the focussing means for the emission light is a telecentric mirror.

10. The spectrophotometer as claimed in claims 6, wherein the means providing the substantially monochromatic emission light is a monochromator.

11. A spectrophotometer comprising:
    a light source;
    a sample position;
    an optical system directing a beam of substantially monochromatic light derived from the light source to a liquid sample when contained in a well when located at the sample position, the well having an internal shape, the optical system comprising:
    (i) an entrance aperture, through which the beam of substantially monochromatic light is derived, followed by a second aperture associated with means providing the substantially monochromatic light,
    (ii) focussing means providing conjugate images of the entrance and second apertures whereby there is established between the conjugate images a region of the beam of substantially monochromatic light that has a particular shape as determined by the shape and size of the conjugate images, and
    (iii) imaging means demagnifying and imaging the region of the beam of light of particular shape into the well for interaction with the liquid sample therein, wherein the particular shape of the region of the beam of light corresponds with the internal shape of the well for substantially all of the liquid sample to be uniformly illuminated without the well obstructing any portion of the beam of light; and
    a detection system detecting light from the liquid sample after interaction of the substantially monochromatic beam of light therewith.

12. A spectrophotometer comprising:
    a light source;
    a sample position;
    an excitation optical system directing a beam of substantially monochromatic light derived from the light source to a liquid sample when contained in a well when located at the sample position; and
    an emission optical system and a detector, the emission optical system directing light emitted from the liquid sample after interaction of the beam of substantially monochromatic light therewith to the detector, the emission optical system comprising:
(i) imaging means providing an image of the bottom surface of the well and an image of the top surface of the liquid sample in the well whereby there is established outside of the well and between the images a region of the emitted light having a shape that is similar to the internal shape of the well,
(ii) focussing means and means providing substantially monochromatic light from the emission light, the focussing means focussing the region of emitted light of similar shape onto the means providing substantially monochromatic light,
the detector arranged to detect the substantially monochromatic emission light from the means for providing such light.

13. The spectrophotometer as claimed in claim 12, wherein the region of the emitted light of similar shape has a substantially constant cross-section.

14. The spectrophotometer as claimed in claim 12, wherein the imaging means providing said images to establish the region of emitted light of similar shape is an off-axis ellipsoidal mirror.

15. The spectrophotometer as claimed in claim 12, wherein the focussing means is a telecentric mirror.

16. The spectrophotometer as claimed in claim 12, wherein the means providing the substantially monochromatic emission light is a monochromator.

* * * * *